(12) United States Patent
Liu et al.

(10) Patent No.: US 9,151,153 B2
(45) Date of Patent: Oct. 6, 2015

(54) CRYSTAL SENSOR MADE BY ION IMPLANTATION FOR SENSING A PROPERTY OF INTEREST WITHIN A BOREHOLE IN THE EARTH

(75) Inventors: Yi Liu, Houston, TX (US); Othon Monteiro, Houston, TX (US); Kerry L. Sanderlin, Houston, TX (US); Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 653 days.

(21) Appl. No.: 13/307,801

(22) Filed: Nov. 30, 2011

(65) Prior Publication Data

US 2013/0134981 A1     May 30, 2013

(51) Int. Cl.
| | |
|---|---|
| *G01V 3/20* | (2006.01) |
| *E21B 47/10* | (2012.01) |
| *G01N 29/02* | (2006.01) |
| *G01N 29/24* | (2006.01) |
| *E21B 47/12* | (2012.01) |
| *E21B 49/10* | (2006.01) |

(52) U.S. Cl.
CPC ............... *E21B 47/101* (2013.01); *E21B 47/12* (2013.01); *E21B 49/10* (2013.01); *G01N 29/022* (2013.01); *G01N 29/2437* (2013.01)

(58) Field of Classification Search
CPC ....... E21B 47/101; E21B 47/12; E21B 49/10; G01N 29/022; G01N 29/2437
USPC .................................. 324/324, 355
See application file for complete search history.

(56) References Cited

U.S. PATENT DOCUMENTS

| | | | | |
|---|---|---|---|---|
| 4,471,255 | A * | 9/1984 | Mikoshiba et al. | ....... 310/313 R |
| 4,510,671 | A | 4/1985 | Kurtz et al. | |
| 5,402,031 | A * | 3/1995 | Tagami et al. | ................. 310/359 |
| 5,633,616 | A * | 5/1997 | Goto | ............................. 333/193 |
| 5,734,105 | A * | 3/1998 | Mizukoshi | ................. 73/504.02 |
| 5,801,069 | A * | 9/1998 | Harada et al. | ................... 438/52 |
| 6,070,463 | A * | 6/2000 | Moriya et al. | ............. 73/504.12 |
| 6,489,616 | B2 | 12/2002 | Giedd | |
| 7,401,525 | B2 | 7/2008 | Cobianu et al. | |
| 8,450,904 | B2 * | 5/2013 | Iwamoto et al. | .......... 310/313 R |
| 8,631,702 | B2 * | 1/2014 | Horning et al. | ............. 73/504.13 |
| 2003/0117237 | A1 * | 6/2003 | Niu et al. | ....................... 333/187 |

(Continued)

FOREIGN PATENT DOCUMENTS

| | | | |
|---|---|---|---|
| DE | 196 36 461 A1 * | 3/1998 | |
| EP | 0072744 A2 | 2/1983 | |

OTHER PUBLICATIONS

Avigal et al., The nature of ion-implanted contacts to polycrystalline diamond films; Apr. 22, 2004; Science Direct; Diamond and related materials 13; pp. 1674-1679.*

(Continued)

*Primary Examiner* — Jay Patidar
(74) *Attorney, Agent, or Firm* — Cantor Colburn LLP

(57) ABSTRACT

Disclosed is a method for producing a crystal sensor. The method includes selecting a crystal configured to sense a property of interest. The method further includes implanting ions in the crystal using ion-implantation to produce a conductive region within the crystal where the conductive region is capable of providing a signal to sense the property of interest. Also disclosed is a method and apparatus for estimating a property of interest using the crystal sensor in a borehole penetrating the earth.

19 Claims, 5 Drawing Sheets

(56) References Cited

U.S. PATENT DOCUMENTS

| | | |
|---|---|---|
| 2006/0207087 A1* | 9/2006 | Jafri et al. .................. 29/831 |
| 2009/0100925 A1* | 4/2009 | DiFoggio et al. ............. 73/32 A |
| 2009/0194830 A1* | 8/2009 | Ransley et al. ............... 257/415 |
| 2010/0052472 A1* | 3/2010 | Nishino et al. ............ 310/313 D |
| 2011/0128003 A1 | 6/2011 | Thompson et al. |
| 2011/0304346 A1* | 12/2011 | DiFoggio et al. ............. 324/633 |
| 2012/0049691 A1* | 3/2012 | Kando et al. ............. 310/313 C |
| 2013/0063149 A1* | 3/2013 | Reittinger et al. ............ 324/324 |
| 2014/0068931 A1* | 3/2014 | Horning et al. ................ 29/825 |
| 2014/0175945 A1* | 6/2014 | Kando ........................ 310/321 |

OTHER PUBLICATIONS

Liu et al.; Measurement of density and viscocity of dodecane and decane with a piezoelectric tuning fork over 298-448K and 0.1-137.9 MPa; 2011; Sensors and Actuators A 167; Physical; pp. 347-353.*
Notification of Transmittal of the International Search Report and the Written Opinion of the International Searching Authority, or the Declaration; PCT/US2012/064623; Mar. 29, 2013.

* cited by examiner

CRYSTAL SENSOR MADE BY ION IMPLANTATION FOR SENSING A PROPERTY OF INTEREST WITHIN A BOREHOLE IN THE EARTH

BACKGROUND

Crystal sensors are known in the earth drilling industry for being able to characterize fluids while deep in a borehole. In one example, a flexural mechanical resonator is made of a piezoelectric crystal in the shape of a tuning fork having two or more electrodes. By applying an alternating voltage to the electrodes at one or more frequencies, the flexural mechanical resonator resonates in a fluid of interest with an electrical impedance related a fluid characteristic. It is known how to relate the measured impedance to fluid characteristics such as density, viscosity and dielectric constant for example.

The two or more electrodes are typically deposited on a surface of the piezoelectric crystal. Unfortunately, such a crystal sensor can fail due to exposure to fluids at high temperatures, such as 200° C. or greater, high pressure, and chemicals that can attack it. In order to provide a level of protection to the electrodes, some crystal sensors include a thin protection layer of dielectric material over the electrodes. However, the thin protection layer can also fail, which leads to the electrodes being exposed to the fluids again. Hence, it would be well received in the drilling industry if the reliability of crystal sensors could be improved.

BRIEF SUMMARY

Disclosed is a method for producing a crystal sensor. The method includes selecting a crystal configured to sense a property of interest. The method further includes implanting ions in the crystal using ion-implantation to produce a conductive region within the crystal where the conductive region is capable of providing a signal to sense the property of interest.

Also disclosed is a method for estimating a property of interest downhole. The method includes: conveying a carrier through a borehole penetrating the earth; placing a crystal disposed at the carrier in communication with the property of interest, the crystal having a conductive region within the crystal, the conductive region being produced by ion-implantation and configured to provide a signal related to the property; and estimating the property using the signal.

Further disclosed is an apparatus for estimating a property of interest downhole. The apparatus includes: a carrier configured to be conveyed through a borehole penetrating an earth formation; a crystal disposed at the carrier and configured to be in communication with the property of interest, the crystal having a conductive region within the crystal, the conductive region being produced by ion-implantation and configured to provide a signal related to the property; and a processor configured to receive the signal to estimate the property.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Figure 1:
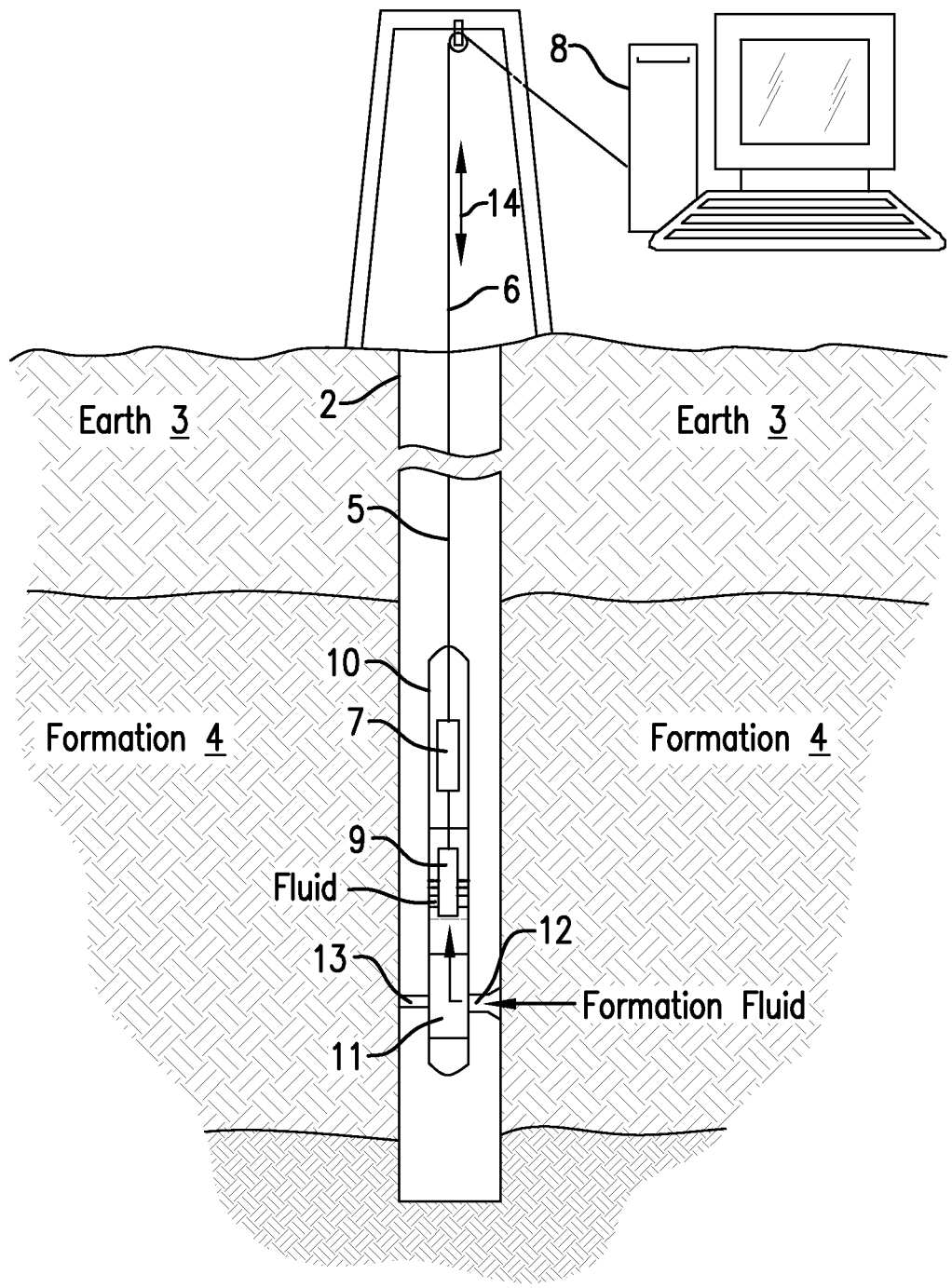
FIG. 1 illustrates an exemplary embodiment of a downhole tool having a crystal sensor disposed in a borehole penetrating the earth.

FIG. 1 illustrates an exemplary embodiment of a downhole tool 10 disposed in a borehole 2 penetrating the earth 3, which includes an earth formation 4. The formation 4 represents any subsurface material of interest such as a formation fluid. The downhole tool 10 is conveyed through the borehole 2 by a carrier 5. In the embodiment of FIG. 1, the carrier 5 is an armored wireline 6. Besides supporting the downhole tool 10 in the borehole 2, the wireline 6 can also provide communications 14 between the downhole tool 10 and a computer processing system 8 disposed at the surface of the earth 3. Communications can include sending measurement data uphole to the system 8 or commands downhole to the tool 10. In logging-while-drilling (LWD) or measurement-while-drilling (MWD) embodiments, the carrier 5 can be a drill string. In order to operate the downhole tool 10 and/or provide a communications interface with the surface computer processing system 8, the downhole tool 10 includes downhole electronics 7.

Still referring to FIG. 1, the downhole tool 10 is configured to perform a measurement of a property of interest of a fluid downhole using a crystal sensor 9. The fluid of interest can be a formation fluid extracted from the formation 4 or a borehole fluid present in the borehole 2. In order to extract the formation fluid from the formation 4, the downhole tool 10 includes a formation fluid tester 11. The formation fluid tester 11 is configured to extend a probe 12 from the tester 11 to seal with a wall of the borehole 2. A brace 13 may be extended in order to keep the probe 12 in contact with the borehole wall. Pressure is then lowered in the probe 12 to cause a sample of the formation fluid to flow into the tester 12. Once the sample is extracted from the formation 4, the crystal sensor 9 is immersed in the sample to perform a measurement of a property of the fluid sample. In another embodiment, a sample of a borehole fluid is extracted from the borehole 2 and the crystal sensor 9 is immersed in that sample to measure a property of the borehole fluid.

Figure 2A:
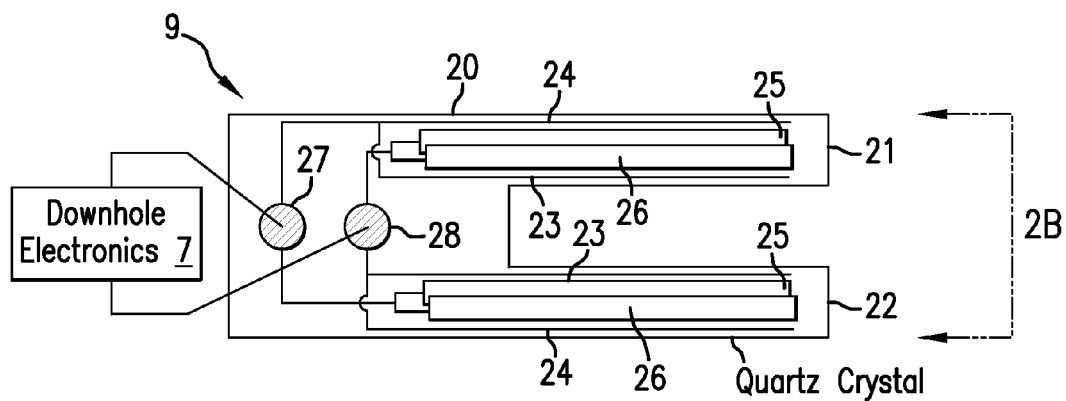
FIGS. 2A and 2B, collectively referred to as FIG. 2, depict aspects of the crystal sensor that is a flexural mechanical resonator.
Figure 2B:
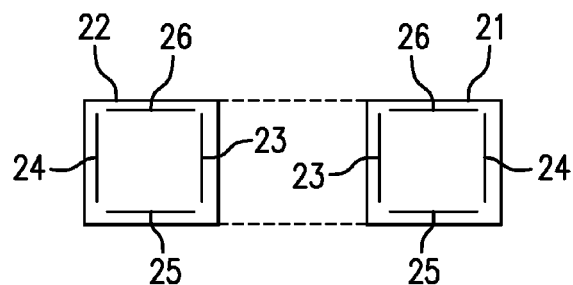

Reference may now be had to FIG. 2, which depicts aspects of one embodiment of the crystal sensor 9. In the embodiment of FIG. 2, the crystal sensor 9 is a piezoelectric flexural mechanical resonator 20, which may be referred to as the piezoelectric resonator 20. The piezoelectric resonator 20 is fabricated from a piezoelectric crystal and has a shape configured to resonate or vibrate in a fluid of interest. In a non-limiting embodiment, the piezoelectric crystal is a quartz crystal. In the embodiment illustrated in FIG. 2A, the piezoelectric resonator 20 is shaped as a tuning fork having a first tine 21 and a second tine 22, which resonate at a resonate frequency. Embedded in each of the tines are a first electrode 23, a second electrode 24, a third electrode 25 and a fourth electrode 26. The electrodes are generally positioned in such a way that deformation of the crystal tines occurs when an electric field is applied to the electrodes. FIG. 2B illustrates an end view of the quartz tuning fork depicting an arrangement of the electrodes 23-26. Because the electrodes 23-26 are conductive, they may be referred to as conductive regions 23-26, respectively. The conductive regions 23-26 have higher conductivity that the piezoelectric crystal causing electric fields in the piezoelectric crystal when a voltage is applied to the appropriate electrodes. The piezoelectric resonator 20 will mechanically flex (i.e., resonate or vibrate) at a frequency f in response to an electrical stimulus applied by the electrodes 23-26 to the piezoelectric crystal. The electrical stimulus is applied by the downhole electronics 7 to the electrodes 23-26 via contact pads 27 and 28. In general, the contact pads are recessed in the crystal host when the conductive regions are subsurface to the crystal host. It can be appreciated that other types of piezoelectric crystals with various shapes and appropriate electrode arrangements may be used in the crystal sensor 9 for various modes of operation (e.g., longitudinal mode, thickness shear mode, flexural mode, and face shear mode) For example, in one or more embodiments, the crystal sensor 9 may have two electrodes in each time and the piezoelectric crystal can be lithium niobate ($LiNbO_3$). Other non-limiting embodiments of the piezoelectric crystal include lead zirconate titanate (PZT), lithium tantalite, lithium borate, berlinite, gallium arsenide, lithium tetraborate, aluminum phosphate, bismuth germanium oxide, polycrystalline zirconium titanate ceramics, high alumina ceramics, silicon zinc oxide composite, and dipotassium tartrate.

When a voltage with a sweeping frequency is applied to a pair of the electrodes, an electric field is created within the piezoelectric material 20 causing the piezoelectric resonator 20 to resonate or vibrate at a resonant frequency and a resonant factor Q related to a property of the fluid in which the sensing portion is immersed. The resonating of the piezoelectric resonator 20 displaces or causes motion of the fluid in which it is immersed, thus, coupling the resonator 20 to that fluid. That is, the fluid experiences alternating displacements or motions as the piezoelectric resonator 20 resonates. During sensing of the property, a pair of electrodes presents an electrical impedance, referred to as a motion impedance, due the resonating or vibrating. The motion impedance has a value related to a mechanical, physical, or electrical property of the fluid of interest. Non-limiting examples of the property include temperature, pressure, density, viscosity, and dielectric constant. While impedance measurements at the resonant frequency may present a signal with a higher signal to noise ratio, measurements can also be performed at other frequencies.

Figure 3:
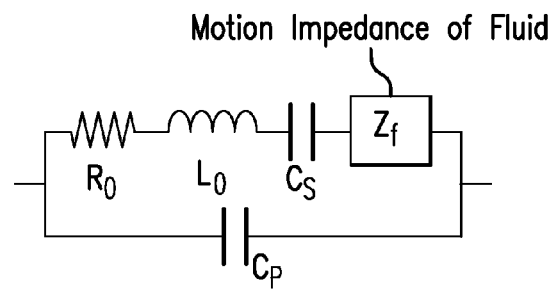
FIG. 3 depicts aspects of an equivalent circuit representing the flexural mechanical resonator.

FIG. 3 illustrates an equivalent electrical circuit representing the piezoelectric resonator 20 where $Z_f(Z_f=R_f+iX_f)$ represents the motion impedance of the fluid of interest and, thus, a mechanical property of the fluid of interest. $C_P$ is the parallel capacitance. $R_0$, $L_0$, and $C_s$ are the equivalent series resistance, inductance and capacitance that simulate the electromechanical resonance of a piezoelectric resonator. They correspond to the friction, mass and compliance, respectively, in the mechanical resonator model. The $R_0$ is the friction term of the resonator, including electric resistance and mechanical friction. For a sensitive measurement of $R_f$, the resistance $R_0$ should be on the order of or less than $R_f$. In one embodiment of a tuning fork resonator, $R_0$ is about 10 KΩ, mainly form mechanical friction, and $R_f$ is at least on the order of 10 KΩ. Thus, the conductive regions providing the electrodes are configured to provide a total resistance on the order or 10 KΩ or less.

Figure 4:
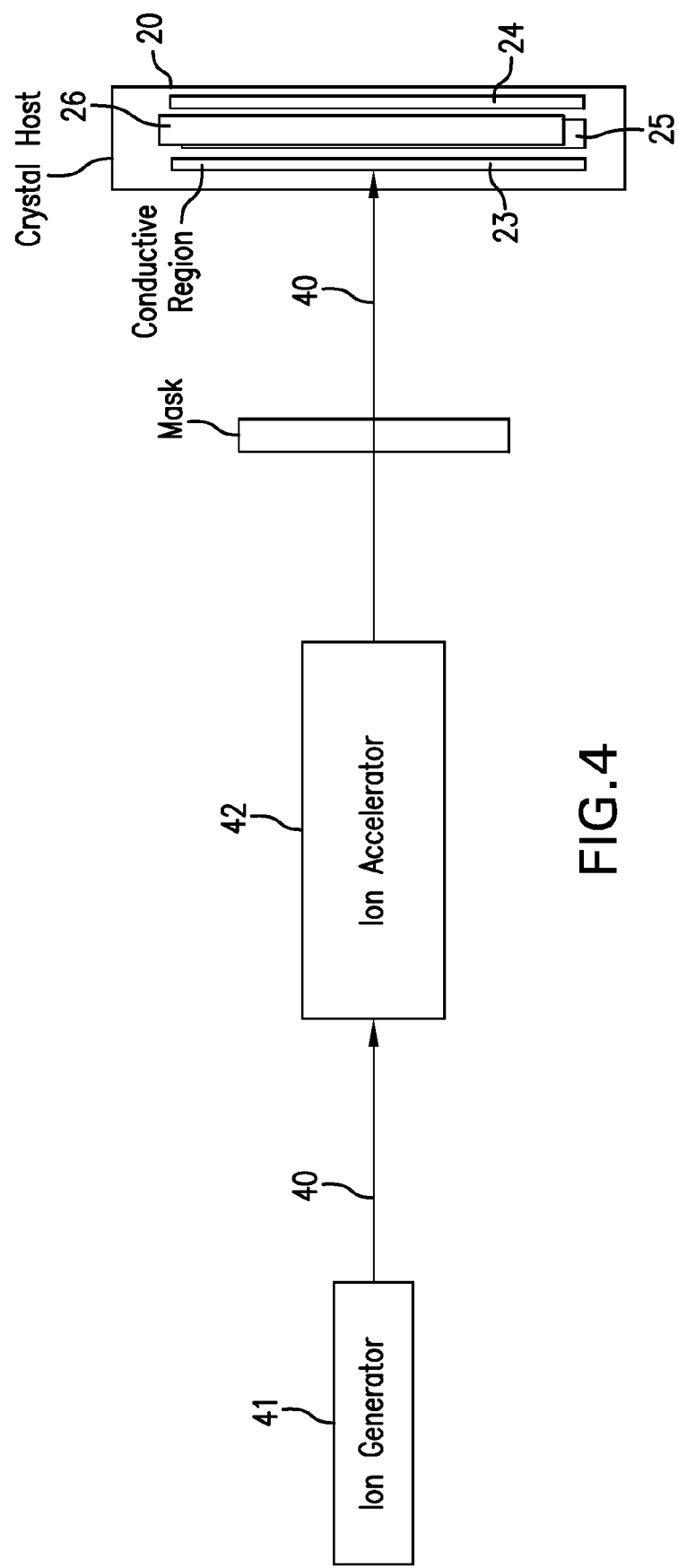
FIG. 4 depicts aspects of implanting ions in a crystal to build the crystal sensor.

In order to prevent fluids from damaging the conductive regions 23-26, such as by abrasion or chemical attack, the conductive regions 23-26 are embedded within the piezoelectric crystal by ion-implantation. That is, the conductive regions 23-26 are deposited inside of the piezoelectric crystal such that the conductive regions 23-26 are enclosed or surrounded by the piezoelectric crystal. It can be appreciated that ion implantation precludes electrodes being disposed on the surface of the piezoelectric crystal and then being covered by a protection layer, which can be unreliable in a downhole environment. FIG. 4 depicts aspects of ion-implantation of a piezoelectric crystal. An ion generator 41 generates ions 40 of material (i.e., dopants) used to dope the crystal host to form the conductive regions 23-26. An ion accelerator 42 accelerates the generated ions to a high energy or speed. The high energy ions then impact the crystal and are embedded in the crystal. The depth of penetration of the dopants depends on the crystal material, the dopants, and energy to which the dopant ions are accelerated. In one or more embodiments, the dopant ions are accelerated to energies in a range from a few keV to several MeV that results in penetration depths of about less than 1 nm to 10 μm or more in a quartz crystal.

The desired conductivity of the conductive regions 23-26 can be achieved by the introduction of point defects (e.g., oxygen vacancies), introduction of exogenous atoms, or structural damage (amorphizaton) due to the ion-implantation. Changes to the crystal lattice include formation of deep or shallow level defects in the energy band gap of electrons or holes in the lattice structure and/or phase separation of a conducting layer within the piezoelectric crystal. When the crystal material is doped with donor or acceptor impurities, impurity energy levels are introduced between the valence band and the conduction band. The added impurity atoms modify the Fermi level. The thermally excited electrons or holes can be current carriers with high conductivity when the Fermi level is close to the conduction band or valence band. By controlling the incident ion energy and the ion dose (i.e., fluence), a specific composition or defect profile results within the crystal to create conductive regions. The implanted conductive regions will have differentiated electrical properties with respect to the crystal host. The desired geometry and/or electrical characteristics of the conductive regions can be implemented by implanting the dopant ions in accordance with a mask fabricated using lithographic techniques such as those used in the fabrication of semiconductors and integrated circuits.

It can be appreciated that the conductive regions 23-26 can be conductive or semi-conductive with respect to crystal depending on the geometry of the conductive region, the dopant ion material, and crystal material. A conductive region that is semi-conductive will conduct electrons or holes if the electrons or holes receive enough energy to span the energy gap between the valence band and the conduction band to become free electrons or holes. Hence, a conductive region that may be non-conductive at room temperature may be conductive at the ambient high temperatures, such as 200° C. or greater, present in a downhole environment.

It can be appreciated that various types of ion dopants may be used depending on the desired electrical characteristics to be achieved in a conductive region and the type of crystal host material. Non-limiting embodiments of ion species for implantation in a crystal include arsenic, phosphorus, boron, boron difluoride, indium, antimony, germanium, silicon, nitrogen, hydrogen, and helium.

In one or more embodiments, after the dopant ions are implanted, the piezoelectric crystal may be "annealed." "Annealing" relates to heating the implanted crystal to a high temperature where the resulting vibrations of interstitial dopant ions causes these dopant ions to be "shaken" into lattice positions in the lattice structure. Thus, the thermal annealing may improve the damage or dopant profile and induce partial recrystallization within the crystal host. In one or more non-limiting embodiments, thermal annealing of a doped crystal is performed in a temperature range of 700° C. to 800° C.

In order to prevent "leakage" of the implanted ions from the host crystal, more of the crystal material can be grown on top of ion implanted areas using methods such as chemical vapor deposition (CVD) or molecular beam epitaxy (MBE) in one or more embodiments.

As illustrated in FIG. 2, each conductive region includes a contact pad for connection to the downhole electronics 7. In one or more embodiments, the contact pads are formed by removing crystal material from the crystal host and depositing a metal layer upon a portion of the corresponding conductive region. The crystal material can be removed by drilling or etching as non-limiting examples. In one or more embodiments, ion-beam mixing is used to enhance the electrical conductivity and adhesion between the metal layer of each contact pad and the crystal host. In ion-beam mixing, apparatus similar to the apparatus illustrated in FIG. 4 for ion-implantation is used to bombard each of the metal layers with ion radiation in order to promote mixing of metal layer material and conductive region material at the interface.

It can be appreciated that while in one or more embodiments the crystal sensor 9 is configured as a flexural mechanical resonator as discussed above, the crystal sensor 9 can also have other configurations in other embodiments. In one or more embodiments, the crystal sensor 9 is configured as a thickness shear mode (TSM) resonator, a mechanical resonator, a bar bender resonator, a disk bender resonator, a cantilever resonator or a torsion resonator. In general, TSM resonators measure the viscosity density product of the fluid of interest. In one or more embodiments, the crystal sensor 9 is configured to measure temperature. As a temperature sensor, a conduction region operates as a semi-conductor such that an increase in temperature results in an increase of free electrons or holes. The increase in free electrons or holes alters an electrical characteristic of the of the conduction region, which can be correlated or calibrated to a change in temperature. In one or more embodiments, the crystal sensor 9 is configured to measure a force, acceleration, stress or strain. In these embodiments, the property being measured causes a distortion or elastic deformation of the lattice of the crystal, which in turn causes a change in an electrical characteristic of one or more conduction regions. The change in the electrical characteristic can be correlated or calibrated to the property of interest that caused the distortion or elastic deformation of the crystal lattice. In one or more embodiments, the crystal sensor 9 can be configured to measure gravitational acceleration by coupling a proof mass to the crystal, which can be shaped as a cantilever for example. In these gravimeter embodiments, the force of gravity acting on the proof mass causes the elastic deformation of the crystal lattice (i.e., bending of the cantilever) leading to a change in an electrical characteristic in the conductive region.

It can be appreciated that in embodiments of the crystal sensor 9 not requiring a piezoelectric crystal material for use in a resonator, other types of crystal material can be used such as silicon in a non-limiting embodiment.

It can be appreciated that output from the crystal sensor 9 can be correlated to the property of interest being sensed or measured by analysis and/or calibration to a known reference standard.

Figure 5:
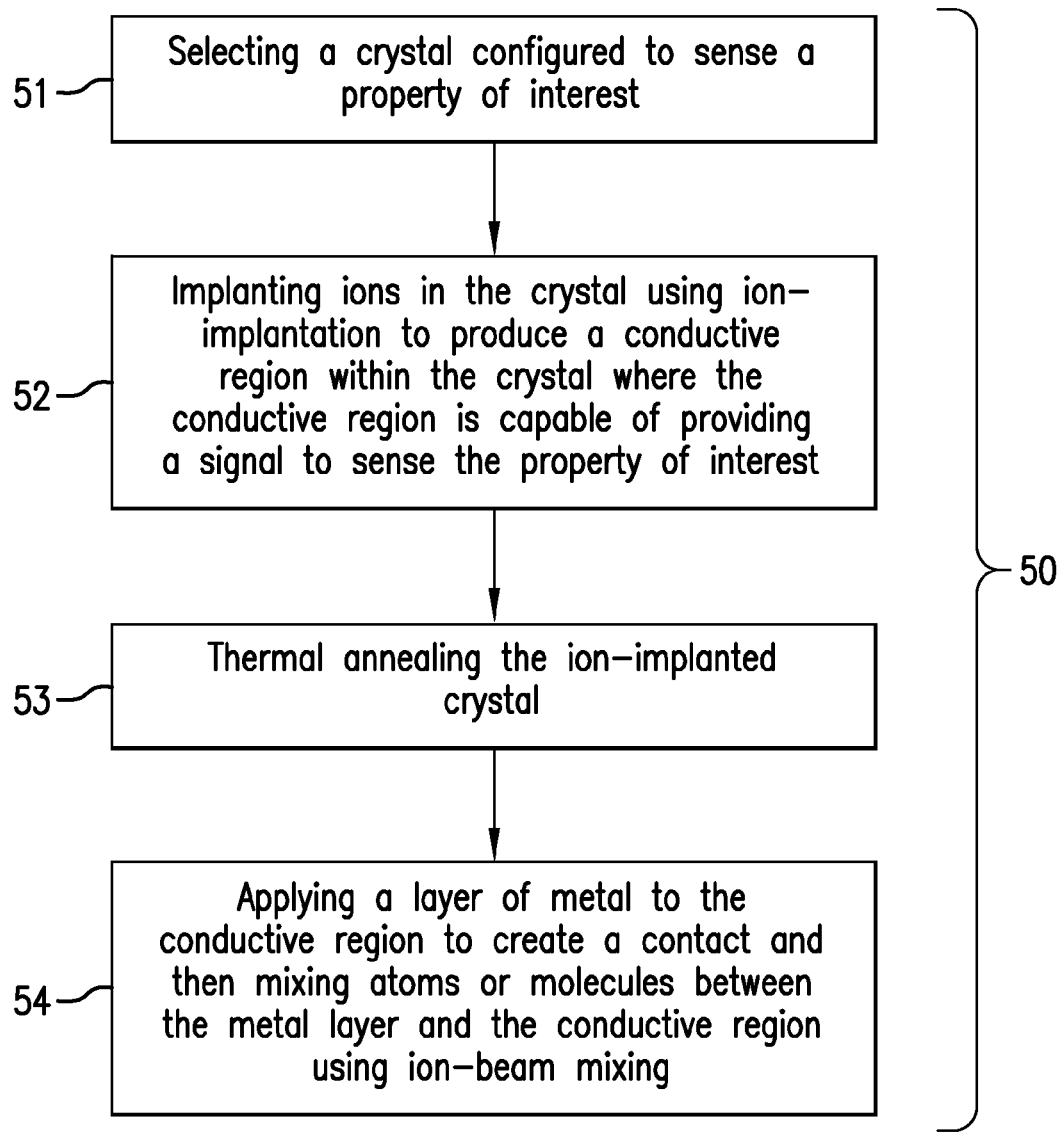
FIG. 5 is a flow chart of a method for producing the crystal sensor using ion-implantation.

FIG. 5 presents one example of a method 50 for producing a crystal sensor. The method 50 calls for (step 51) selecting a crystal configured to sense a property of interest. Step 51 can include selecting an appropriate shape and/or crystal material, such as a piezoelectric crystal material, for sensing the property of interest. Further, the method 50 calls for (step 52) implanting ions with appropriate energy in the crystal using ion-implantation to produce a conductive region within the crystal where the conductive region is capable of providing a signal to sense the property of interest. Step 52 can include selecting appropriate ion dopants for providing the desired electrical characteristics for sensing the property of interest. Further, the method 50 calls for (step 53) thermal annealing the ion-implanted crystal. Further, the method 50 calls for (step 54) applying a layer of metal to the conductive region to create a contact pad and then mixing atoms or molecules between the metal layer and the conductive region using ion-beam mixing.

Figure 6:
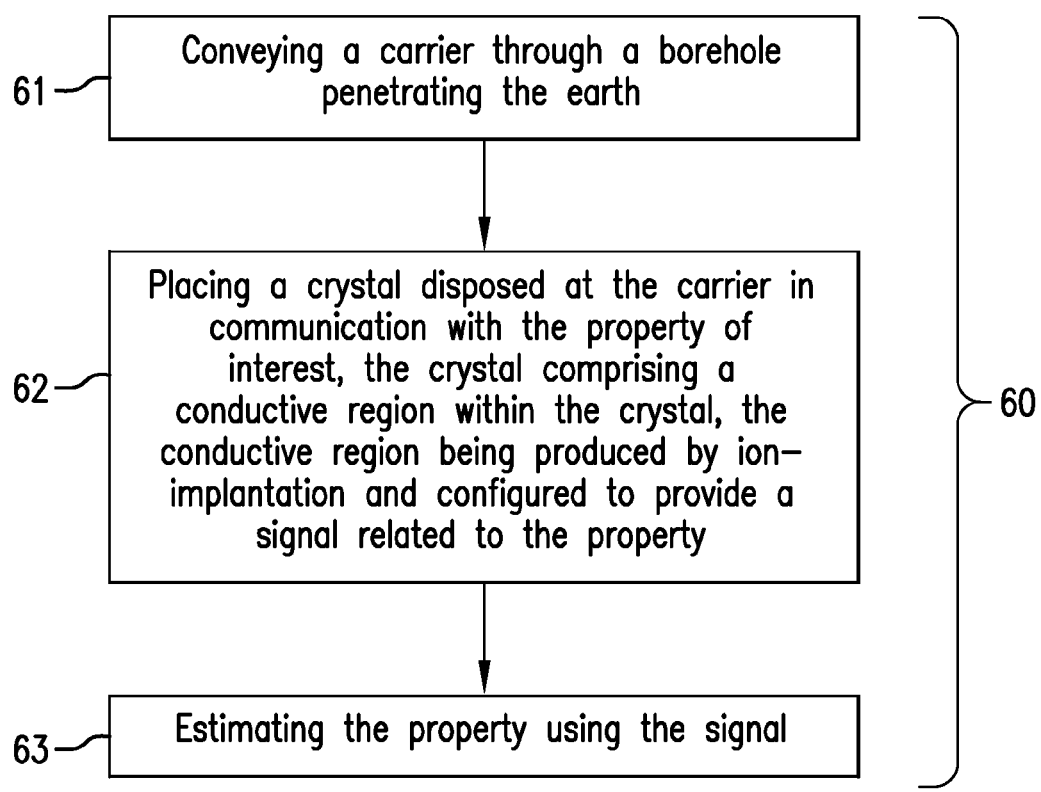
FIG. 6 is a flow chart of a method for estimating a property of interest in the borehole.

FIG. 6 presents one example of a method 60 for estimating a property of interest downhole. The method 60 calls for (step 61) conveying a carrier through a borehole penetrating the earth. Further, the method 60 calls for (step 62) placing a crystal disposed at the carrier in communication with the property of interest, the crystal comprising a conductive region within the crystal, the conductive region being produced by ion-implantation and configured to provide a signal related to the property. Further, the method 60 calls for (step 63) estimating the property using the signal.

In support of the teachings herein, various analysis components may be used, including a digital and/or an analog system. For example, the downhole electronics 7 or the surface computer processing 8 may include the digital and/or analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of non-transitory computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order. The term "couple" relates to coupling a first component to a second component either directly or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for producing a sensor for sensing a property of interest of a downhole fluid, the method comprising: selecting a piezoelectric flexural resonator to sense the property of interest of the down hole fluid, the piezoelectric flexural resonator comprising a piezoelectric crystal to be in communication with the downhole fluid; implanting ions in the piezoelectric crystal using ion-implantation to produce a conductive region within the crystal; coupling the piezoelectric flexural resonator to a carrier to be conveyed through a borehole penetrating the earth; and the conductive region providing a signal to sense the property of interest of the downhole fluid.

2. The method according to claim 1, wherein the piezoelectric crystal comprises quartz, PZT, lithium niobate, lithium tantalite, lithium borate, berlinite, gallium arsenide, lithium tetraborate, aluminum phosphate, bismuth germanium oxide, polycrystalline zirconium titanate ceramics, high alumina ceramics, silicon zinc oxide composite, or dipotassium tartrate.

3. The method according to claim 1, wherein the conductive region comprises at least one electrode.

4. The method according to claim 3, wherein the at least one electrode comprises two or more electrodes electrically insulated from each other.

5. The method according to claim 4, wherein the piezoelectric crystal comprises a shape configured to resonate within a fluid when alternating voltage is applied to the two or more electrodes at one or more frequencies.

6. The method according to claim 5, wherein the shape comprises a tuning fork.

7. The method according to claim 1, further comprising removing crystal material to access a portion of the conductive region.

8. The method according to claim 7, further comprising applying a metal layer to the portion of the conductive region to form a contact pad.

9. The method according to claim 8, further comprising adhering the metal layer to the portion of the conductive region using ion beam mixing.

10. The method according to claim 1, wherein implanting ions comprises thermal annealing of the crystal.

11. The method according to claim 1, wherein implanting ions comprises producing a mask using lithography and performing the ion-implantation according to the mask.

12. The method according to claim 1, further comprising applying one or more lattice layers of a same material of the crystal over a surface of the crystal through which the ion-implantation was conducted.

13. A method for estimating a property of interest of a downhole fluid, the method comprising:
conveying a carrier through a borehole penetrating the earth, a piezoelectric flexural resonator being disposed on the carrier, the piezoelectric flexural resonator comprising a piezoelectric crystal;
placing the piezoelectric crystal in communication with the downhole fluid, the crystal comprising a conductive region within the crystal, the conductive region comprising implanted ions and provides a signal related to the property of interest of the downhole fluid; and
estimating the property using the signal.

14. The method according to claim 13, further comprising applying a voltage to the conductive region.

15. An apparatus for estimating a property of interest of downhole fluid, the apparatus comprising: a carrier to be conveyed through a borehole penetrating an earth formation; a piezoelectric flexural resonator disposed on the carrier and comprising a piezoelectric crystal to be in communication with the downhole fluid, the crystal comprising a conductive region within the crystal, the conductive region comprising implanted ions and provides signal related to the property of interest of the downhole fluid; and a processor to receive the signal to estimate the property of interest of the downhole fluid.

16. The apparatus according to claim 15, wherein the conductive region is coupled to a contact pad.

17. The apparatus according to claim 16, wherein the crystal is configured to vibrate in a fluid upon an alternating voltage being applied to the contact pad.

18. The apparatus according to claim 15, wherein the conductive region is configured to conduct electrical charges upon the conductive region receiving energy related to sensing the property of interest in order to estimate the property of interest.

19. The apparatus according to claim 15, wherein the carrier comprises a wireline, a slickline, a drill string, or coiled tubing.

* * * * *